(12) United States Patent
Phan

(10) Patent No.: US 10,251,788 B1
(45) Date of Patent: Apr. 9, 2019

(54) ASSISTING THE VISUALLY IMPAIRED

(71) Applicant: Dylan Phan, Garland, TX (US)

(72) Inventor: Dylan Phan, Garland, TX (US)

( * ) Notice: Subject to any disclaimer, the term of this patent is extended or adjusted under 35 U.S.C. 154(b) by 0 days.

(21) Appl. No.: 15/796,972

(22) Filed: Oct. 30, 2017

(51) Int. Cl.
| *A61F 9/08* | (2006.01) |
| *A61H 3/06* | (2006.01) |
| *G01S 15/46* | (2006.01) |
| *G01S 15/58* | (2006.01) |
| *G01S 17/46* | (2006.01) |
| *G01S 17/58* | (2006.01) |
| *G09B 21/00* | (2006.01) |

(52) U.S. Cl.
CPC ............... *A61F 9/08* (2013.01); *G01S 15/46* (2013.01); *G01S 15/58* (2013.01); *G01S 17/46* (2013.01); *G01S 17/58* (2013.01); *G09B 21/003* (2013.01); *G09B 21/006* (2013.01); *A61H 3/061* (2013.01); *A61H 2003/063* (2013.01); *A61H 2201/5064* (2013.01); *A61H 2201/5079* (2013.01); *A61H 2201/5084* (2013.01)

(58) Field of Classification Search
CPC .. G08B 21/02; A61H 2201/165; A61H 3/061; A61H 3/068; A61F 9/08; G01S 15/46
USPC ................................................ 340/4.1, 686.6
See application file for complete search history.

(56) References Cited

U.S. PATENT DOCUMENTS

| 6,298,010 B1 * | 10/2001 | Ritz | A61H 3/061 367/116 |
| 7,755,744 B1 * | 7/2010 | Leberer | G01C 3/08 356/5.1 |
| 7,778,112 B2 * | 8/2010 | Behm | A61H 3/061 135/911 |
| 7,855,657 B2 * | 12/2010 | Doemens | A61H 3/061 340/4.11 |
| 8,696,357 B2 * | 4/2014 | AlDossary | G09B 21/001 434/114 |
| 2012/0119920 A1 * | 5/2012 | Sallop | A43B 3/0005 340/686.6 |
| 2015/0049325 A1 * | 2/2015 | Curtis | G01S 17/93 356/4.01 |
| 2015/0356837 A1 * | 12/2015 | Pajestka | A61H 3/061 340/4.14 |
| 2018/0078444 A1 * | 3/2018 | Gamerman | A61H 3/061 |
| 2018/0110672 A1 * | 4/2018 | Kasravi | A61H 3/061 |

* cited by examiner

*Primary Examiner* — Emily C Terrell
(74) *Attorney, Agent, or Firm* — Baker Botts L.L.P.

(57) ABSTRACT

A system for assisting the visually impaired comprises one or more distance sensors, one or more electronic storage devices, one or more processors, and an output component. The one or more distance sensors are configured to make distance measurements between the distance sensor and one or more objects, the one or more electronic storage devices are operable to store boundaries defining a three-dimensional space, the one or more processors are communicatively coupled to the distance sensors and the electronic storage devices and are operable to receive distance measurements from the distance sensors and generate output signals related to the received distance measurements within the defined three-dimensional space. The output component is further operable to receive the output signals from the one or more processors and convert the output signals into a non-visual user output related to the received distance measurements.

20 Claims, 4 Drawing Sheets

ASSISTING THE VISUALLY IMPAIRED

TECHNICAL FIELD

This disclosure relates generally to assisting the visual impaired, and specifically to assisting the visually impaired by identifying objects and their distances in an environment.

BACKGROUND

Some tasks, such as walking, may be difficult for persons who are visually impaired. Although accommodations have been developed to assist the visually impaired with such tasks, the conventional accommodations may be associated with certain disadvantages. For example, walking assistance provided by seeing-persons and/or service animals does not offer independence to the visually-impaired and may in some cases be associated with perpetual expenses. As another example, walking canes or sticks provide limited assistance and may, in some cases, be a liability and may draw unwanted attention to the visually impaired.

SUMMARY OF THE DISCLOSURE

According to one embodiment, a system for assisting the visually impaired comprises one or more distance sensors, one or more electronic storage devices, one or more processors, and an output component. The one or more distance sensors are configured to make distance measurements between the one or more distance sensors and one or more objects, wherein the one or more distance sensors measure distance based on at least one of a set comprising: electromagnetic waves and ultrasonic waves. The one or more electronic storage devices are operable to store boundaries defining a three-dimensional space. The one or more processors are communicatively coupled to the one or more distance sensors and the one or more electronic storage devices, the one or more processors are operable to receive distance measurements from the one or more distance sensors, determine the speed of the one or more objects based on the received distance measurements, determine the acceleration of the one or more objects based on the received distance measurements, and determine the direction of the one or more objects based on the received distance measurements. The one or more processors are further operable to generate output signals related to the received distance measurements within the defined three-dimensional space and generate alert signals based on one or more of the detected speed, acceleration, and distance of an object. The output component is operable to receive the output signals from the one or more processors and convert the output signals into a non-visual user output related to the received distance measurements for the defined three-dimensional space. The output component is further operable to receive one or more alert signals from the one or more processors and generate one or more outputs associated with the received one or more alert signals. The output component being a tactile interface comprising a two-dimensional array of output points that communicate non-visual output through one or more from the set comprising: pressure and temperature. The output component having a refresh rate and a resolution, and wherein one or more of the following are adjustable: the boundaries defining the three-dimensional space; the refresh rate of the output component; the resolution of the output component; and the relationship between the received distance measurements and the generated output signals.

According to another embodiment, a system for assisting the visually impaired comprises one or more distance sensors, one or more electronic storage devices, one or more processors, and an output component. The one or more distance sensors are configured to make distance measurements between the distance sensor and one or more objects, the one or more electronic storage devices are operable to store boundaries defining a three-dimensional space, the one or more processors are communicatively coupled to the one or more distance sensors and the one or more electronic storage devices and are operable to receive distance measurements from the one or more distance sensors and generate output signals related to the received distance measurements within the defined three-dimensional space. The output component is operable to receive the output signals from the one or more processors and convert the output signals into a non-visual user output related to the received distance measurements.

Certain embodiments of the present disclosure may provide one or more technical advantages.

One advantage of the present disclosure is converting distance information of surrounding objects to a visually-impaired individual through an interface into a format interpretable to the visually-impaired individual.

Another advantage allows for the notification of fast-moving and potentially dangerous surrounding objects to a visually-impaired individual through an interface in a format interpretable to the visually-impaired individual.

Still another advantage is the ability to modify the boundaries of the surrounding area depicted to a visually-impaired individual through an interface in a format interpretable to the visually-impaired individual, as well as the refresh rate and resolution of the interface, to suit the needs of the particular individual and situation.

One or more other technical advantages may be readily apparent to one skilled in the art from the figures, descriptions, and claims, included herein. Moreover, while specific advantages have been enumerated above, various embodiments may include all, some, or none of the enumerated advantages.

BRIEF DESCRIPTION OF THE DRAWINGS

For a more complete understanding of the present disclosure and for further features and advantages thereof, reference is now made to the following description taken in conjunction with the accompanying drawings, in which.

DETAILED DESCRIPTION OF THE DISCLOSURE

Embodiments of the present disclosure and its advantages are best understood by referring to FIGS. 1-4, like numerals being used for like and corresponding parts of the various drawings.

The system of the present disclosure provides information about objects in the environment of a user with a visual-impairment (e.g., blindness) through a non-visual output interpretable by the user. As an example, a non-visual output may be an array of adjustable pressure outputs worn by the user. Each pressure output functions like a pixel in a visual display and the number of pressure outputs creates a resolution similar to the number of pixels in a visual display, and the rate the pressure output updates information creates a refresh rate similar to the refresh rates in a visual display (e.g., 4000 hz). The pressure outputs may communicate the location and movement of objects in a user's environment to the user, thereby allowing the user to better understand and navigate their environment.

Because a user's ability to differentiate pressure signals may not be as great as a user's ability to differentiate visual signals, the resolution of a tactile output may not be the same as the resolution of a visual display. Similarly, a tactile output must contact the user and may not be the same size as a visual display. Due to the limitations of non-visual output (e.g., tactile or auditory outputs), the system may include a defined three-dimensional space to be output to the user. The limited scope of the defined three-dimensional space allows details of objects within the defined three-dimensional space to be communicated to the user through the non-visual output in greater detail than if a larger space had to be reported.

A non-visual output may alert users of objects outside the defined three-dimensional space in certain circumstances. For example, sensors of the system may detect an object that is outside the defined three-dimensional space and a processor may determine that the object is fast moving and approaching the user, then generate an alert to an output (e.g., auditory or tactile) to notify the user of potential danger. Alerts allow the system to provide user information about only certain objects outside the defined three-dimensional space at certain times, thereby minimizing the burden to the limited non-visual output. In some cases, a user may configure the device to generate an alert in specific circumstances.

A sensor of the system may be placed anywhere on a user. This disclosure recognizes that wearing a sensor on the head allows a user to move their head and the field of view of the sensor in a similar fashion to how a person without visual impairment would survey their environment. The output of the system through, for example, a tactile interface, may change as a user moves their head and the view of the attached sensor.

Figure 1:
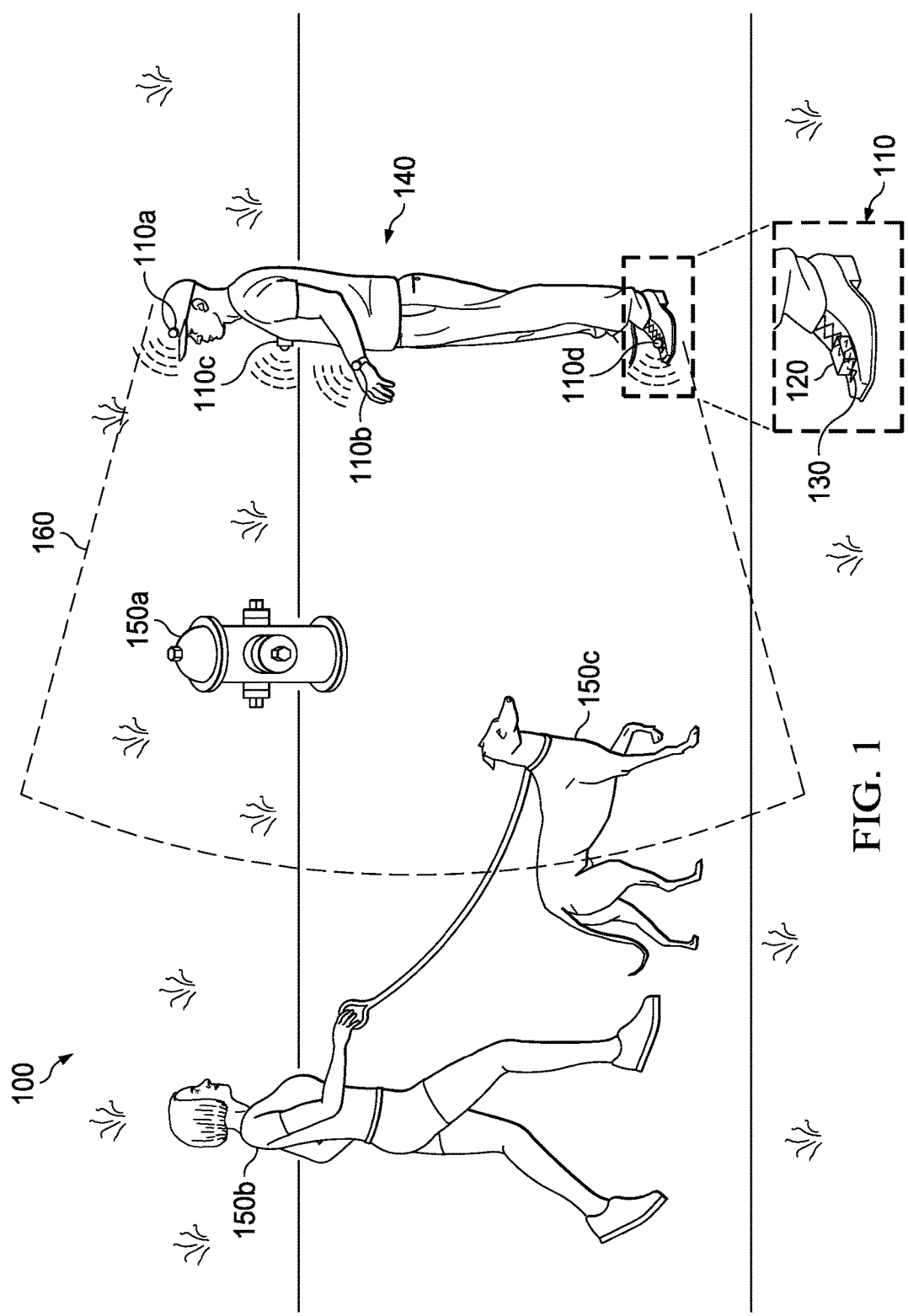
FIG. 1 illustrates an example of a system for assisting the visually impaired in an environment, according to certain embodiments.

FIG. 1 illustrates an example of a system 110 for assisting the visually impaired in an environment 100. System 110 may be configured to detect information about objects 150 in environment 100 and notify a device user 140 of the identified information.

In some embodiments, system 110 includes a device 120 and a fastener 130. As discussed in more detail with respect to FIG. 2, device 120 may include one or more of a processor, an electronic storage device, a communication interface, a user interface, a sensor, and an output component. Fastener 130 is configured to couple device 120 to the device user 140. As depicted in FIG. 1, fastener 130 may be a shoelace threaded through holes on device 120 and through eyelets of a shoe of device user 140. In other embodiments, fastener 130 may include or be one or more of bolts, buttons, buckles, ties, clamps, clasps, nails, pegs, and/or screws. Fasteners 130 may be any other suitable component that couples device 120 to device user 140 or an article of device user 140.

FIG. 1 illustrates system 110 being deployed on a hat (110a), as a wristband (110b), on a pocket of a shirt (110c), and on a shoe (110d). As illustrated in FIG. 1, device 110 may be configured to detect information about objects 150 in environment 100 such as fire hydrant 150a, dog walker 150b, and/or dog 150c. Generally, device user 140 may employ system 110 when moving around in environment 100 and be notified, via alerts, when an object 150 is detected in environment 100.

In certain embodiments, system 110 may include a defined three-dimensional space 160. Three-dimensional space 160 may be analogized to a "field of view" for user 140 provided by system 110. Three-dimensional space 160 may be defined in any suitable fashion, for example, using one or more of distances relative to user 140, angles relative to user 140, GPS coordinates, or any other suitable definition. The boundaries of three-dimensional space 160 may be stored in an electronic storage device of system 110 and may be adjustable, for example, by user 140. In particular embodiments, an output component (e.g., output component 110a) of system 110 may only output information about objects within three-dimensional space 160. An output component may generate alerts for objects 150 detected outside three-dimensional space 160. For example, an output component of a two-dimensional array of pressure outputs (e.g., a pin board) may output information to user 140 about objects 150 within three-dimensional space 160. However, sensors of system 110 may detect objects outside of three-dimensional space 160 and system 110 may generate alerts to user 140 of objects 150 (e.g., potentially dangerous objects 150).

Defined three-dimensional space 160 prevents user 140 from being overwhelmed by information communicated through system 110. Defined three-dimensional space 160 also allows the limited resolution of an output component (e.g., the number of pins in an array of pressure outputs) to describe objects 150 near user 140 with more precision because the output does not also have to describe objects 150 further away. Alerts allow system 110 to notify users 140 of objects 150 outside three-dimensional space 160 (e.g., a car approaching at high speed towards the user).

Adjusting the boundaries of three-dimensional space 160 allows user 140 (or system 110 if automated) to optimize outputs for different environments. For example, a crowded urban sidewalk may be better navigated defining a three-dimensional space 160 close to user 140, while a park may be better navigated defining a three-dimensional space 160 that includes area further away from user 140 and at wider angles to user 140.

In certain embodiments, the relationship between the distance measurements from sensors and the output of an output component may be adjustable, for example, by user 140. For example, user 140 may adjust one or more of the amplitude or frequency of output signals from an output component 110 based on one or more of the distance, speed, location, acceleration, position, and estimated path of an object 150. In an embodiment, fast moving objects 150 may output as closer to user 140 on output component 110 to allow reaction time to the fast moving object 150. In another example, objects 150 outside three-dimensional space 160 that have an estimated path to intersect three-dimensional space 160 may be output as within three-dimensional space 160 before the object enters three-dimensional space 160 to allow user 140 to react.

Figure 2:
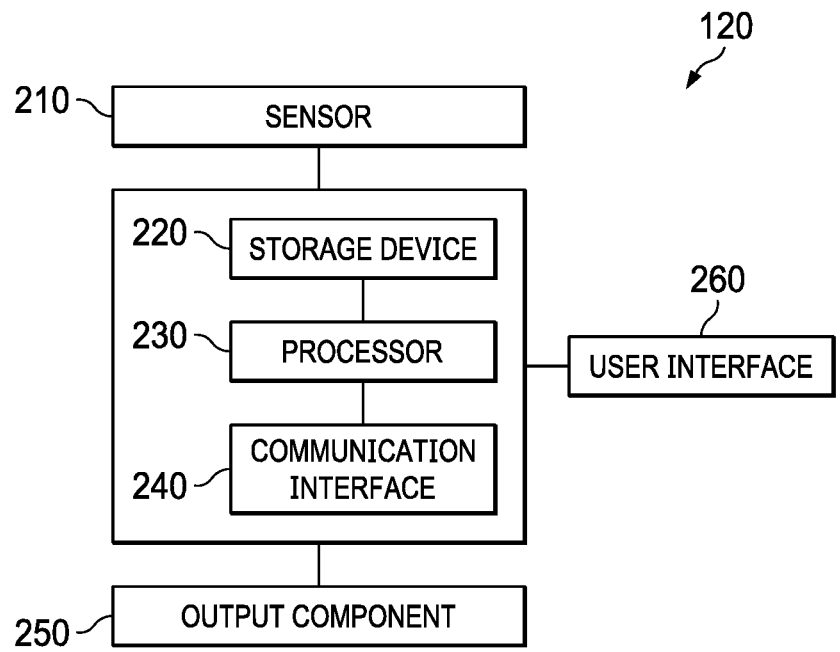
FIG. 2 illustrates a block diagram of the system of FIG. 1, according to one embodiment.

FIG. 2 illustrates one embodiment of device 120. As depicted in FIG. 2, device 120 may comprise one or more of sensor 210, electronic storage device 220, processor 230, communication interface 240, output component 250, and user interface 260. Although this disclosure describes and depicts device 120 having one of each sensor 210, electronic storage device 220, processor 230, communication interface 240, output component 250, and user interface 260, this disclosure recognizes that device 120 may have as many of each component as suitable or desired. In some embodiments, device 120 includes some but not all of the components depicted in FIG. 2. This disclosure further recognizes that components of device 120 may not be included in a single case and may be discrete communicatively coupled components.

Sensors 210 may be configured to measure distance to one or more objects 150 in environment 100, for example, the distance between sensor 210 and an object 150. Detectable objects 150 may be mobile or stationary. As an example, sensors 210 may be configured to detect data about stationary fire hydrant 150a and/or mobile dog walker 150b and dog 150c of FIG. 1. Detectable information may include one or more of the presence of object 150 in environment 100, a speed of object 150, an acceleration of object 150, a direction of object 150, and a position of object 150 in the environment. Sensors 210 may utilize one or more of ultrasonic and electromagnetic waves to measure distance. In certain embodiments, sensors 210 include one or more of a camera, an infrared sensor, an ultraviolet sensor, and an ultrasonic sensor.

In some embodiments, sensors 210 operate asynchronously (e.g., an infrared sensor operates at a first time and an ultraviolet sensor operates at a second time). In other embodiments, the one or more sensors 210 work in parallel or simultaneously (e.g., both the infrared sensor and ultraviolet sensor operate at a first time and all sensor types operate at a second time). Which sensors 210, or combination of sensors 210, that are active may be adjustable, for example, by user 140. This disclosure recognizes that the most accurate information about objects 150 may result when all sensor types operate simultaneously at all times to detect information about objects 150. In some embodiments, sensors 210 may have a particular refresh rate. As used herein, a refresh rate refers to the frequency at which information about object 150 is detected and/or communicated to processor 230. Sensors 210 may also have a resolution, for example, the maximum number of pixels for a digital image from a camera.

As illustrated in FIG. 2, device 120 includes one or more electronic storage devices 220. Although this disclosure describes and depicts device 120 as having only a single electronic storage device 220, this disclosure recognizes that device 120 may include any suitable number of electronic storage devices 220 configured to store any suitable information. In some embodiments, electronic storage device 220 is configured to store information to be used by processor 230. Electronic storage device 220 may store information related to safety thresholds for a user 140. For example, electronic storage device 220 may store one or more of threshold distance, speed, acceleration, angle of attack, approximated path, or other suitable information for alerting a visually-impaired user 140 of potentially dangerous objects in environment 100. Thresholds stored in electronic storage device 220 may be relied upon by processor 230 to generate alerts to output component 250 to notify user 140 of such potentially dangerous objects in environment 100. Although this disclosure describes certain types of information that may be stored, this disclosure recognizes that electronic storage device 220 may store any information that may be desirable to be used by processor 230.

As illustrated in FIG. 2, device 120 further includes at least one processor 230. In some embodiments, processor 230 is communicatively coupled to one or more sensors 210, electronic storage devices 220, communication interfaces 240, output components 250, and user interfaces 260. In some embodiments, the information received from sensors 210 includes data about object 150, such as distance measurements to object 150, in environment 100 of device user 140. In some embodiments, processor 230 may further be operable to make determinations about object 150 based on the information received from sensors 210. For example, processor 230 may determine, based on information received from sensors 210, that an object 150 is present in environment 100, if object 150 is moving, and may determine one or more of speed, acceleration, direction, and estimated path of object 150 relative to user 140. Processor 230 may further be operable to compare one or more of the distance, the speed, the acceleration, the direction, and the estimated path of object 150 to threshold values stored in electronic storage device 220 in order to determine whether to generate an alert signal to output component 250 to notify user 140 of potentially dangerous objects 150 in environment 100.

As stated above, processor 230 may further be operable to generate an alert to output component 250 in some embodiments. Output component 250 may generate a non-visual user output in response to receiving alerts from processor 230. In some embodiments, the alert generated by output component 250 is one or more of an auditory alert or a tactile alert. In some other embodiments, an alert may be directed to people other than user 140. For example, in certain embodiments the alert may be a visual alert such as a light and/or a flare emitted from a flare gun. Processor 230 may further be operable to increase or decrease the intensity (e.g., the amplitude or frequency of a tactile or auditory alert). In some embodiments, the intensity of the alert is increased or decreased based on one or more of the location, speed, acceleration, distance, direction, and estimated path of object 150.

For example, processor 230 may generate a first alert having a first intensity in response to determining that the distance between object 150 in environment 100 and sensors 210 at a first time is less than the stored distance value and subsequently generate a second alert having a second intensity in response to determining that the distance between object 150 in environment 100 and sensors 210 at a second time has decreased relative to the distance between object 150 in environment 100 and sensors 210 at the first time. As another example, processor 230 may increase the intensity of an alert in response to determining that the acceleration rate of object 150 at a second time has increased relative to the acceleration rate of object 150 at a first time.

In some embodiments, processor 230 generates a specific type of alert in response to detecting certain characteristics about object 150. For example, processor 230 may generate a tactile alert in response to determining that the distance between object 150 and sensors 210 is less than the distance value stored in storage device 220 but may generate an audio alert or flare alert in response to determining that device user 140 may collide with object 150. Processor 230 may determine that device user 140 may collide with object 150 based on one or more of a distance between object 150 and sensors 210 (e.g., less than 3 feet), an acceleration of object 150 (e.g., greater than 8 miles per hour), and a duration of detection (e.g., detected for more than 1 second).

This disclosure recognizes certain benefits to conveying other types of information about object 150 and relaying that information to device user 140. For example, this disclosure recognizes benefits of conveying more precise location information about object 150 to device user 140. For example, processor 230 may generate an audio alert having a first intensity to convey that object 150 is located to the left of device user's center in environment 100 and generate an audio alert having a second intensity to convey that object 150 is located to the right of device user's center in environment 100. As will be described in more detail below, this disclosure contemplates embodiments wherein device 120 relays information about object 150 to device user 140 in a manner that is comprehensible to device user 140.

Device 120 may also include a communication interface 240 in some embodiments. Communication interface 240 may include hardware, software, or both providing one or more interfaces for communication (such as, for example, packet-based communication) between device 120 and other systems and/or networks. As an example and not by way of limitation, communication interface 240 may include a network interface controller (NIC) or network adapter for communicating with an Ethernet or other wire-based network or a wireless NIC (WNIC) or wireless adapter for communicating with a wireless network, such as a WI-FI network.

This disclosure contemplates any suitable network and any suitable communication interface 240 for it. As an example and not by way of limitation, device 120 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, device 120 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Device 120 may include any suitable communication interface 240 for any of these networks, where appropriate. Although this disclosure describes and illustrates a particular communication interface, this disclosure contemplates any suitable communication interface.

In some embodiments, a manufacturer or other interested person may communicate with device 120 via communication interface 240. An interested person may wish to communicate with device 120 in order to update settings or stored thresholds. For example, an interested person may update values stored in storage device 220 (e.g., thresholds) such as the acceleration value, the distance value, and/or the time value discussed herein. In such an example, interested person may communicate with device 120 over a network to which device 120 is connected in order to update, delete, or add various features and/or settings (e.g., software upgrades).

Device 120 may further include an output component 250. In some embodiments, output component 250 may be a component configured to present an alert to device user 140. In some embodiments, the alert that is presented on output component 250 is the one or more alerts generated by processor 230. Output components 120 may be speakers, tactile devices such as a vibration pad or pinscreens, and/or a flare gun. Although this disclosure describes and depicts certain types of output devices 250, this disclosure recognizes that output component 250 may be any suitable component operable to present an alert.

As depicted in FIG. 2, device 120 may also include a user interface 260 in some embodiments. User interface 260 may permit device user 120 and/or other users or operators to manually update stored values (e.g., the acceleration value, the distance value, and/or the time value), a preferred alert mode, a preferred intensity of alert, and/or any other setting or option of device 120. In this manner, device user 140 or other operator can customize device 120 to fit needs of device user 140.

Figure 3A:
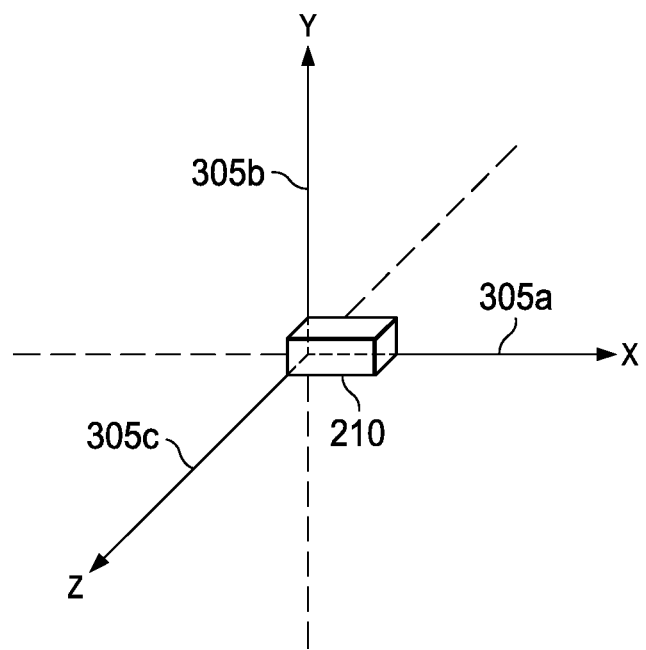
FIG. 3A illustrates an example of a sensor of the system of FIG. 2 detecting information about three axes, according to one embodiment.
Figure 3B:
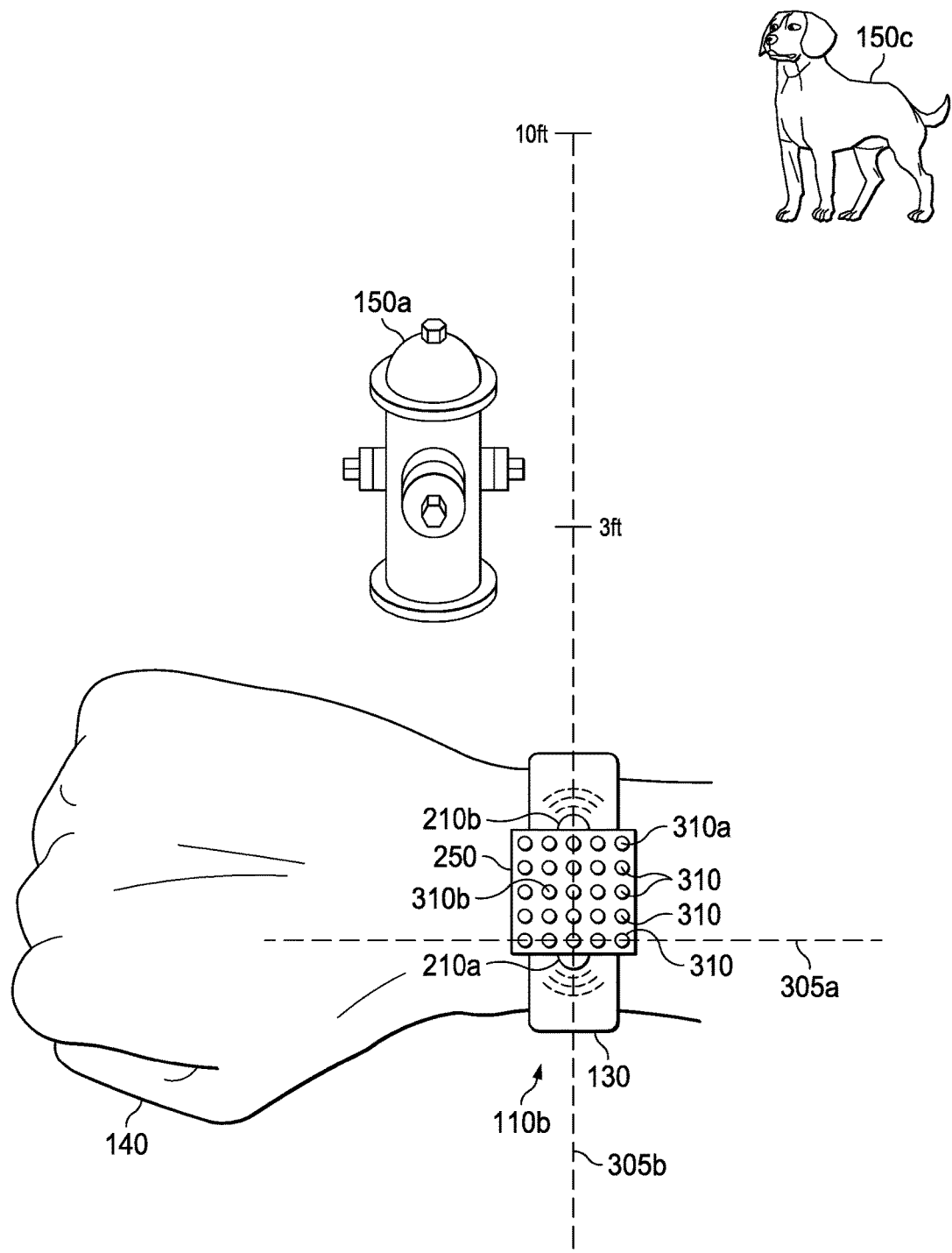
FIG. 3B illustrates an example of the system of FIG. 2 detecting objects in an environment, according to one embodiment.

As described above, device 120 is operable to detect information about objects 150 in environment 100. As depicted in FIGS. 3A-3B, information about position of object 150 may be mapped by device 120 and relayed to device user 140 via output component 250. As shown in FIG. 3A, sensors 210 may be configured to detect information about objects 150 about one or more axes 305. As depicted, sensors 210 may detect information about objects 150 about an x-axis 305a, a y-axis 305b, and a z-axis 305c. As described above, the information sensed by sensors 210 may be relayed to processor 230, which may in turn, relay the information to user 140 through output component 250 in a form that is understandable to user 140.

In some embodiments, such as the embodiment illustrated in FIG. 3B, processor 230 relays information about objects 150 to device user 140 via a pinscreen output component 250. As illustrated, pinscreen output component 250 of FIG. 3B includes a plurality of pins 310 arranged in a two-dimensional array (e.g., a grid or coordinate system that represents environment 100). In the illustrated example, two dimensions of the environment are represented by the x-axis and y-axis of the two-dimensional array and the third-dimension is represented on the z-axis by the amplitude of the output points (e.g., pins) of the pinscreen output component 250. Output component 250 may have a particular refresh rate (e.g., rate at which output component 250 updates with new output) and a particular resolution (e.g., the number of pins in a pinscreen).

In some embodiments, the intersection of axes 305a and 305b define an origin point. The origin point may, in some embodiments, define a position of device 120 and/or one or more sensors 210 or user 140. Pins 310 of pinscreen output component 250 may define objects in environment 100 relative to the origin point. For example, pins 310 along x-axis 305a may define a position in environment 100 to the left or right of the origin point and pins 310 along y-axis 305b may define a position in environment 100 ahead of, or in front of, the origin point. In some embodiments, processor 230 may identify one or more pins 310 of pinscreen output component 250 to represent a position of object 150 in environment 100 and provide instructions to pinscreen output components 250 to depress one or more identified pins 310. This disclosure recognizes that depression of one or more pins 310 may be sensed by device user 140 (e.g., on the wrist of device user 140), who in turn may associate the position of a depressed pin 310 with a position of object 150 in environment 100.

As an example, sensors 210 may detect object 150c in environment 100 and processor may determine, based on the information detected by sensors 210, that object 150c is 10 feet in front of device user 140 (along y-axis 305c) and 3 feet to the right of device user 140 (along x-axis 305a). In such an example, processor 240 may identify pin 310a as representative of the position of object 150c in environment 100. In response to identifying pin 310a as representative of the position of object 150c, processor 240 may send instructions to pinscreen output component 250 to depress pin 310a. As another example, sensors 210 may detect object 150a and send data about object 150a to processor 230. In such an example, processor 230 may determine that object 150a is 3 feet in front of device user 140 (along z-axis 305c) and 1 foot to the left of device user 140 (along x-axis 305a). Based on this determination, processor 230 may identify pin 310b as representative of the position of object 150a in environment 100 and send instructions to pinscreen output component 250 to depress pin 310b.

Figure 4:
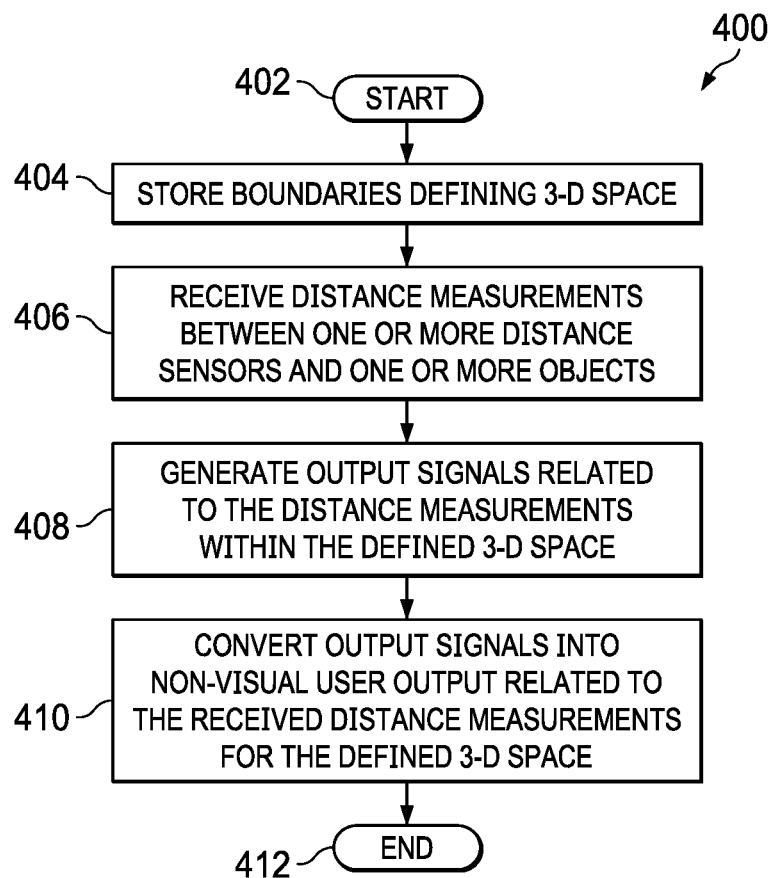
FIG. 4 illustrates a method for assisting the visually impaired using the system of FIG. 2, according to certain embodiments.

FIG. 4 illustrates a method 400 of assisting the visually impaired. In some embodiments, method 400 is performed by device 120 of system 110. In some embodiments, method 400 is an algorithm stored in electronic storage device 220 that may be executable by processor 230. As such, this disclosure recognizes that some or all steps of method 400 may be performed by processor 230 of device 120.

Method 400 begins at a step 402 and continues to a step 404. At step 404, boundaries defining a three-dimensional space are stored (e.g., in one or more electronic storage devices 220). At step 406, distance measurements between one or more distance sensors (e.g., sensors 210) and one or more objects (e.g., objects 150) are received (e.g., from sensors 210). At step 408, output signals related to the received distance measurements within the defined three-dimensional space (e.g., three-dimensional space 160) are generated (e.g., by processor 230). At step 410, interface signals are converted (e.g., by output component 250) into non-visual user output related to the received distance measurements for the defined three-dimensional space (e.g., three-dimensional space 160). Method 400 ends at step 412.

Modifications, additions, or omissions may be made to system 110 without departing from the scope of the disclosure. For example, although one or more components of device 120 have been depicted as a single unit, this disclosure recognizes that components of device 120 may be distributed over body of device user 140 and the components may be communicably coupled to relay information as described herein. For example, sensors 210, storage device 220, and processor 230 may be colocated on a mobile device of device user 140 and output component 250 may be an earpiece operable to present an audio alert to device user 140 in one embodiment. In another embodiment, sensors 210 may be coupled to a hat of device user 140 which relay detected information to processor 220 of a mobile device of user 120. Although the present disclosure has been described with several embodiments, a myriad of changes, variations, alterations, transformations, and modifications may be suggested to one skilled in the art, and it is intended that the present disclosure encompass such changes, variations, alterations, transformations, and modifications as fall within the scope of the appended claims.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, functions, operations, or steps, any of these embodiments may include any combination or permutation of any of the components, elements, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative.

What is claimed is:

1. A system for assisting the visually impaired, the system comprising:
   one or more distance sensors configured to make distance measurements between the distance sensor and one or more objects, wherein the one or more distance sensors measure distance based on at least one of a set comprising: electromagnetic waves and ultrasonic waves;
   one or more electronic storage devices operable to store boundaries defining a three-dimensional space;
   one or more processors communicatively coupled to the one or more distance sensor and the one or more electronic storage devices, the one or more processors operable to:
      receive distance measurements from the one or more distance sensors;
      determine the speed of the one or more objects based on the received distance measurements;
      determine the acceleration of the one or more objects based on the received distance measurements;
      determine the direction of the one or more objects based on the received distance measurements;
      generate output signals based on the received distance measurements for one or more objects within the defined three-dimensional space;
      generate one or more output signals based on the received distance measurements for one or more objects outside the defined three-dimensional space in response to determining that the one or more objects outside the defined three-dimensional space have:
         a direction approaching at least one of the one or more distance sensors; and
         one or more of: a speed exceeding a speed threshold or an acceleration exceeding an acceleration threshold;
   an output component operable to:
      receive the output signals from the one or more processors;
      convert the output signals into non-visual user output wherein:
         the output component is a tactile interface comprising a two-dimensional array of pins that actuate to communicate the non-visual output through pressure and temperature;
         the output component has a refresh rate and a resolution; and one or more of the following are adjustable:
         the boundaries defining the three-dimensional space;
         the refresh rate of the output component;
         the resolution of the output component; and
         the relationship between the received distance measurements and the generated output signals.

2. A system for assisting the visually impaired, comprising:
- one or more distance sensors configured to make distance measurements between the one or more distance sensors and one or more objects;
- one or more electronic storage devices operable to store boundaries defining a three-dimensional space;
- one or more processors communicatively coupled to the one or more distance sensors and the one or more electronic storage devices, the one or more processors operable to:
  - receive distance measurements from the one or more distance sensors; and
  - generate output signals based on the received distance measurements for one or more objects within the defined three-dimensional space;
  - generate one or more output signals related to the received distance measurements for one or more objects outside the defined three-dimensional space in response to determining that the one or more objects outside the defined three-dimensional space have:
    - a direction approaching at least one of the one or more distance sensors; and
    - one or more of: a speed exceeding a speed threshold or an acceleration exceeding an acceleration threshold; and
- an output component operable to:
  - receive the output signals from the one or more processors; and
  - convert the output signals into non-visual user output related to the received distance measurements for the defined three-dimensional space;
- wherein the output component is a tactile interface comprising a two-dimensional array of pins that actuate to communicate the non-visual output through pressure and temperature.

3. The system of claim 2, wherein one or more of the pins is further configured to communicate the non-visual output through one or more from the set comprising: vibration, audio, and electric signals.

4. The system of claim 2, wherein the one or more sensors measure distance based on at least one of a set comprising: electromagnetic waves and ultrasonic waves.

5. The system of claim 2, the output component having a refresh rate and a resolution, and wherein one or more of the following are adjustable:
- the boundaries defining the three-dimensional space;
- the refresh rate of the output component;
- the resolution of the output component; and
- the relationship between the received distance measurements and the generated output signals.

6. The system of claim 2, the one or more processors further operable to:
- determine the speed of objects based on the received distance measurements;
- determine the acceleration of objects based on the received distance measurements; and
- determine the direction of objects based on the received distance measurements.

7. The system of claim 2, wherein the non-visual user output corresponding to the output signals based on the one or more objects within the defined three-dimensional space is perceptively different than the non-visual user output corresponding to the one or more objects outside the defined three-dimensional space.

8. The system of claim 2, wherein:
- the non-visual user output corresponding to the output signals based on the one or more objects within the defined three-dimensional space is communicated via a first pressure and a first temperature;
- the non-visual user output corresponding to the output signals based on the one or more objects outside the defined three-dimensional space is communicated via a second pressure and a second temperature; and
- the first pressure is not equivalent to the second pressure and the first temperature is not equivalent to the second temperature.

9. A device for assisting the visually impaired, the device comprising:
- one or more distance sensors configured to make distance measurements between the one or more distance sensors and one or more objects;
- one or more electronic storage devices operable to store boundaries defining a three-dimensional space;
- one or more processors communicatively coupled to the one or more distance sensors and the one or more electronic storage devices, the one or more processors operable to:
  - receive distance measurements from the one or more distance sensors; and
  - generating output signals based on the received distance measurements for one or more objects within the defined three-dimensional space;
  - generate one or more output signals based on the received distance measurements for one or more objects outside the defined three-dimensional space in response to determining that the one or more objects outside the defined three-dimensional space have:
    - a direction approaching at least one of the one or more distance sensors; and
    - one or more of: a speed exceeding a speed threshold or an acceleration exceeding an acceleration threshold; and
- an output component operable to:
  - receive the output signals from the one or more processors; and
  - convert the output signals into non-visual user output related to the received distance measurements for the defined three-dimensional space;
- wherein the output component is a tactile interface comprising a two-dimensional array of pins that actuate to communicate the non-visual output through pressure and temperature.

10. The device of claim 9, wherein one or more of the pins are farther configured to communicate the non-visual output through one or more from the set comprising: vibration, audio, and electric signals.

11. The device of claim 9, wherein the one or more sensors measure distance based on at least one of a set comprising: electromagnetic waves and ultrasonic waves.

12. The device of claim 9, the output component having a refresh rate and a resolution, and wherein one or more of the following are adjustable:
- the boundaries defining the three-dimensional space;
- the refresh rate of the output component;
- the resolution of the output component; and
- the relationship between the received distance measurements and the generated output signals.

13. The device of claim 9, the one or more processors further operable to:
- determine the speed of objects based on the received distance measurements;

determine the acceleration of objects based on the received distance measurements; and determine the direction of objects based on the received distance measurements.

14. The device of claim 9, wherein the non-visual user output corresponding to the output signals based on the one or more objects within the defined three-dimensional space is perceptively different than the non-visual user output corresponding to the one or more objects outside the defined three-dimensional space.

15. The system of claim 9, wherein:

the non-visual user output corresponding to the output signals based on the one or more objects within the defined three-dimensional space is communicated via a first pressure and a first temperature;

the non-visual user output corresponding to the output signals based on the one or more objects outside the defined three-dimensional space is communicated via a second pressure and a second temperature; and the first pressure is not equivalent to the second pressure and the first temperature is not equivalent to the second temperature.

16. A method for assisting the visually impaired, comprising:

storing boundaries defining a three-dimensional space in one or more electronic storage devices;

receiving, by one or more processors, distance measurements between one or more distance sensors and one or more objects;

generating, by the one or more processors, output signals based on the received distance measurements for one or more objects within the defined three-dimensional space;

generating, by the one or more processors, one or more output signals based on the received distance measurements for one or more objects outside the defined three-dimensional space in response to determining that the one or more objects outside the defined three-dimensional space have:

a direction approaching at least one of the one or more distance sensors; and one or more of: a speed exceeding a speed threshold or an acceleration exceeding an acceleration threshold;

converting, at the output component, the received output signals into non-visual user output related to the received distance measurements for the defined three-dimensional space;

wherein the output component is a tactile interface comprising a two-dimensional array of pins that actuate to communicate the non-visual output through pressure and temperature.

17. The method of claim 16, wherein one or more of the pins are further configured to communicate the non-visual output through one or more from the set comprising: vibration, audio, and electric signals.

18. The method of claim 16, wherein the output component has a refresh rate and a resolution, and wherein one or more of the following are adjustable:

the boundaries defining the three-dimensional space;

the refresh rate of the output component;

the resolution of the output component; and the relationship between the received distance measurements and the generated output signals.

19. The method of claim 16, further comprising one or more of the set comprising:

determining the speed of objects based on the received distance measurements;

determining the acceleration of objects based on the received distance measurements; and determining the direction of objects based on the received distance measurements.

20. The method of claim 16, wherein the non-visual user output corresponding to the output signals based on the one or more objects within the defined three-dimensional space is perceptively different than the non-visual user output corresponding to the one or more objects outside the defined three-dimensional space.

* * * * *